(12) United States Patent
Trintchouk et al.

(10) Patent No.: US 11,900,595 B2
(45) Date of Patent: Feb. 13, 2024

(54) IMAGING SYSTEMS AND METHODS USEFUL FOR PATTERNED STRUCTURES

(71) Applicant: Singular Genomics Systems, Inc., La Jolla, CA (US)

(72) Inventors: Fedor Trintchouk, San Diego, CA (US); Eli N. Glezer, Del Mar, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 425 days.

(21) Appl. No.: 17/308,848

(22) Filed: May 5, 2021

(65) Prior Publication Data

US 2021/0350533 A1 Nov. 11, 2021

Related U.S. Application Data

(60) Provisional application No. 63/021,913, filed on May 8, 2020.

(51) Int. Cl.

| G06K 9/00 | (2022.01) |
| G01N 23/223 | (2006.01) |
| G06T 7/00 | (2017.01) |
| G16B 30/00 | (2019.01) |
| G06T 3/00 | (2006.01) |
| G06T 7/33 | (2017.01) |

(52) U.S. Cl.
CPC .......... *G06T 7/0012* (2013.01); *G06T 3/0075* (2013.01); *G06T 7/33* (2017.01); *G16B 30/00* (2019.02); *G06F 2218/08* (2023.01)

(58) Field of Classification Search
CPC ........ G06K 9/00; G01N 23/223; A61B 6/483; G06T 7/00

USPC ....... 382/100, 103, 106, 128–134, 162, 168, 382/181, 193, 199, 209, 216, 224, 254, 382/276, 286, 305, 294, 312; 250/305; 506/26; 378/4, 6, 21

See application file for complete search history.

(56) References Cited

U.S. PATENT DOCUMENTS

| 10,100,347 | B2* | 10/2018 | Otwinowski | C12Q 1/6855 |
| 2013/0261027 | A1* | 10/2013 | Li | C12N 9/1252 506/26 |
| 2016/0032380 | A1* | 2/2016 | Craighead | C07H 21/00 250/305 |
| 2017/0167979 | A1* | 6/2017 | Rulison | G02B 3/0062 |
| 2021/0114029 | A1* | 4/2021 | Yellen | C12M 23/16 |

OTHER PUBLICATIONS

Bentley et al. (2008). "Accurate whole human genome sequencing using reversible terminator chemistry." Nature 456, 53-59. https://doi.org/10.1038/nature07517.
Lyons. R.G. et al. (Mar. 4, 2015). "Estimating synchronization signal phase." Proc. SPIE 9409, Media Watermarking, Security, and Forensics 2015; 94090P. 15 pages. https://doi.org/10.1117/12.2083390.
Quinn, B. G. (May 1994). "Estimating Frequency by Interpolation Using Fourier Coefficients." IEEE Transactions on Signal Processing, 42(5), 1264-1268. doi: 10.1109/78.295186.

* cited by examiner

*Primary Examiner* — Seyed H Azarian
(74) *Attorney, Agent, or Firm* — Mintz, Levin, Cohn, Ferris, Glovsky, Popeo, P.C.; Zachary L. Terranova

(57) ABSTRACT

Disclosed herein, inter alia, are methods and systems of image analysis useful for identifying and/or quantifying features in patterns.

16 Claims, 17 Drawing Sheets

FIG. 4B

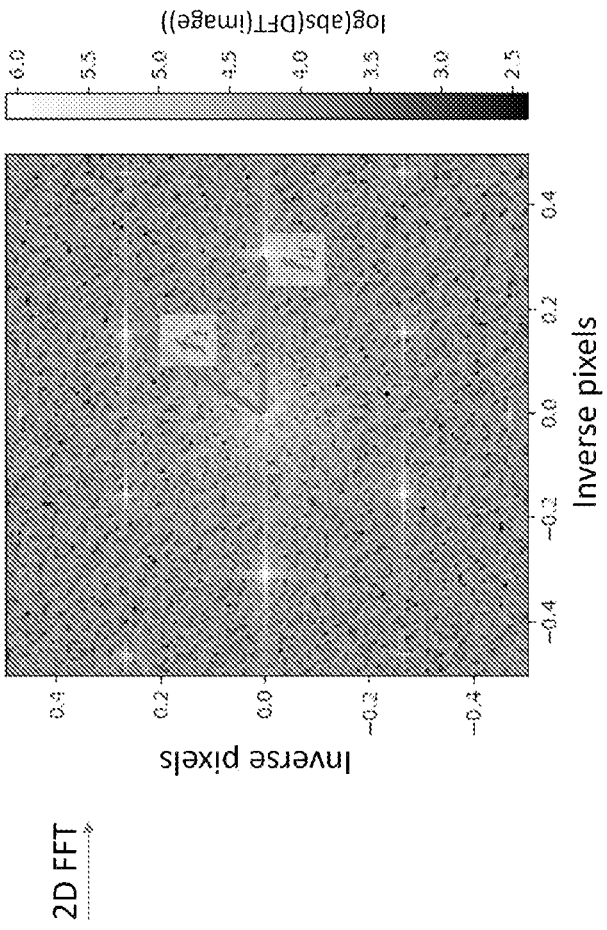
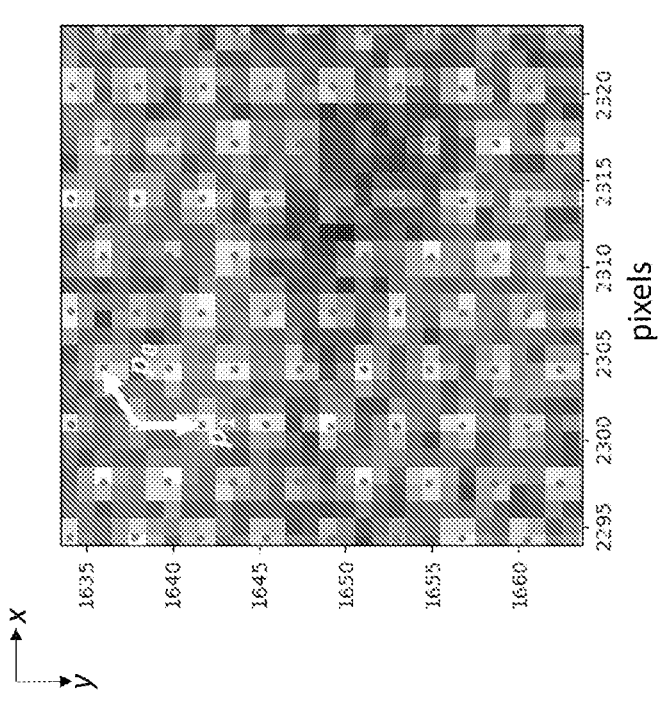

Pixel space, image space

Frequency space, reciprocal space, Fourier space

2D FFT

Lattice is described by primitive vectors $p_0, p_1$
All features addressed by $i*p_0 + j*p_1$ for integer $i, j$ The length of the primitive vector in object space is the pitch. 2 um pitch pattern shown 1 inverse pixel = sampling rate
0.5 inverse pixels = Nyquist rate Reciprocal lattice is described by frequencies $f_0, f_1$
$p_0 \perp f_1, \quad p_1 \perp f_0, \quad [f_0\ f_1]^T = [p_0\ p_1]^{-1}$ Image Registration subimage

IMAGING SYSTEMS AND METHODS USEFUL FOR PATTERNED STRUCTURES

CROSS-REFERENCE TO RELATED APPLICATIONS

This application claims the benefit of U.S. Provisional Application No. 63/021,913, filed May 8, 2020 which is incorporated herein by reference in its entirety and for all purposes.

BACKGROUND

Next generation sequencing (NGS) methods typically rely on the detection of genomic fragments immobilized on an array. For example, in sequencing-by-synthesis (SBS), fluorescently labeled nucleotides are added to an array of polynucleotide primers and are detected upon incorporation. The extension of the nucleic acid primer along a nucleic acid template is monitored to determine the sequence of nucleotides in the template. Each detection event, (i.e., a feature), can be distinguished due to their location in the array.

For these and other applications of polynucleotide arrays, improvements have recently been made to increase density of features in the arrays. Technological advances reduced the typical distance between neighboring features such that the features are only slightly larger than the optical resolution scale, the pixel pitch of the camera, or both. Often, there is significant spatial overlap of fluorescent signal between neighboring features that needs to be considered by the image analysis algorithm. As the size of the features decreases and the overall size of the arrays expand, accurate detection becomes problematic.

BRIEF SUMMARY

Disclosed herein, inter alia, are solutions to the aforementioned and other problems in the art. This disclosure provides methods and systems of image analysis useful for identifying and/or quantifying features in regular patterns. The systems and methods can be used, for example, to register multiple images of a regular pattern of features. In a non-limiting example, the systems and methods are configured to register multiple images of patterns that result from images of arrays used for nucleic acid sequencing.

In an aspect, there is provided a method of quantifying features in a repeating pattern. In a non-limiting example, the method includes the steps of: obtaining an image of an object using a detection apparatus, wherein the image includes a repeating pattern of features having different signal levels; providing the image or image-related data to a computer, wherein the computer has parameter data that describe the repeating pattern of features; partitioning the image or the image-related data into a plurality of registration subimages on the computer; detecting on the computer the repeating pattern of features for each registration subimage and assigning an index address for each feature of the repeating pattern of features; and quantifying a signal level of each feature. The method can further include a step of providing the object wherein the object has a repeating pattern of features in a two-dimensional plane, such as an xy plane. The method can further include a step of providing the object wherein the object has a repeating pattern of features in one or more two-dimensional planes, such as a z-stack of single two-dimensional xy planes. Moreover, one or more of the steps can be performed on the computer using an algorithm stored on computer-readable medium that causes the computer to perform one or more of the steps. In an example, the object is or relates to genomic fragments (e.g., polynucleotides) immobilized on an array.

Also provided is a system that includes a processor; a storage device; and a program including instructions for carrying out or otherwise performing the steps of the above method.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

FIG. 2B shows the focusing beads flattened by the inpainting routine, wherein the intensity of the focusing beads are decreased to within about 1600 counts.

FIG. 4B illustrates the relationships between primitive vectors in an image space and frequency vectors in a reciprocal space, a.k.a. Fourier space or frequency space, respectively.

FIG. 8A shows an image having 4×4 features at different signal levels with different signal levels represented as different colors or shades. FIG. 8B depicts a registration image having 3×3 features. After partitioning the image into a registration image, the image can be analyzed to determine an underlying repeating pattern of features and quantify parameters such as the grid orientation angle, the apparent pitch in pixel units, and the phase of the feature grid at some fixed pixel location, which can all be stored in a matrix in computer memory. After the analysis, each feature can be assigned a unique address, for example, depicted as a two integer vector in a lower right corner for each feature. The unique address is considered as a pair of integers, alternatively referred to as a 2-component integer vector, or and integer vector of length 2.

DETAILED DESCRIPTION

I. Definitions

Figure 1A:
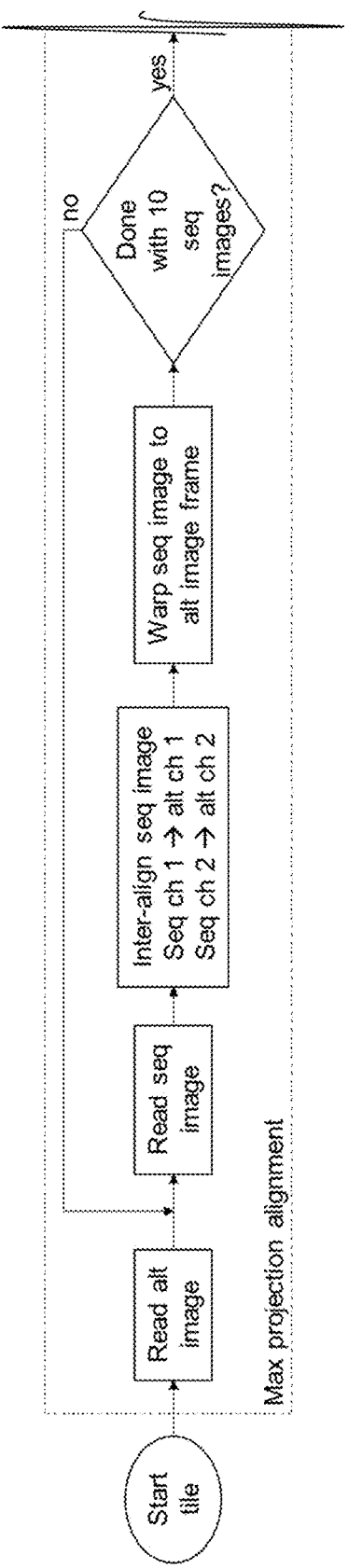
FIGS. 1A-1D show a flow diagram of an exemplary method of processing an image, such as one tile (or subimage) that is at least a portion of the image, to obtain signal levels for one or more features of the tile.
Figure 1B:
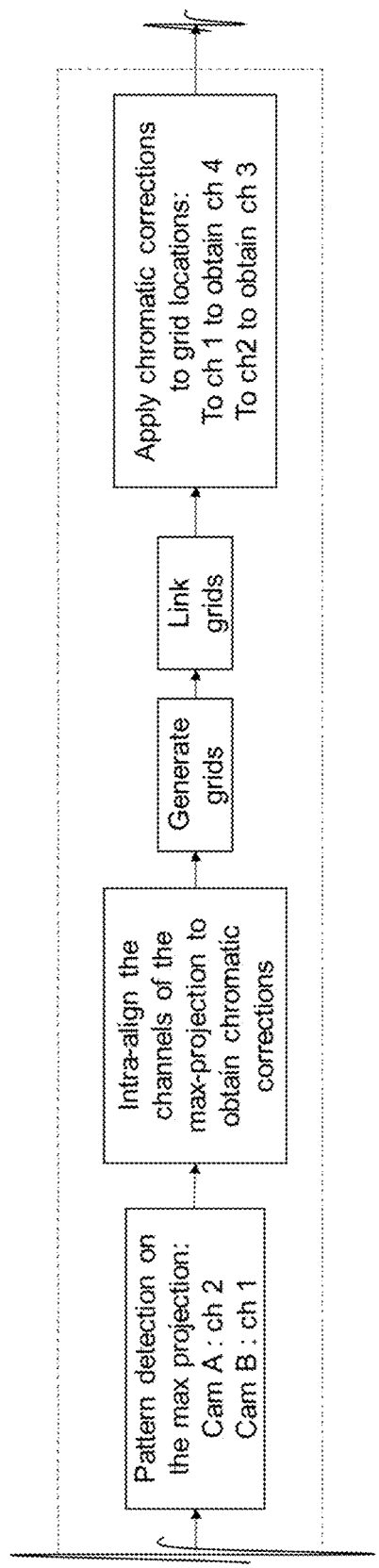
Figure 1C:
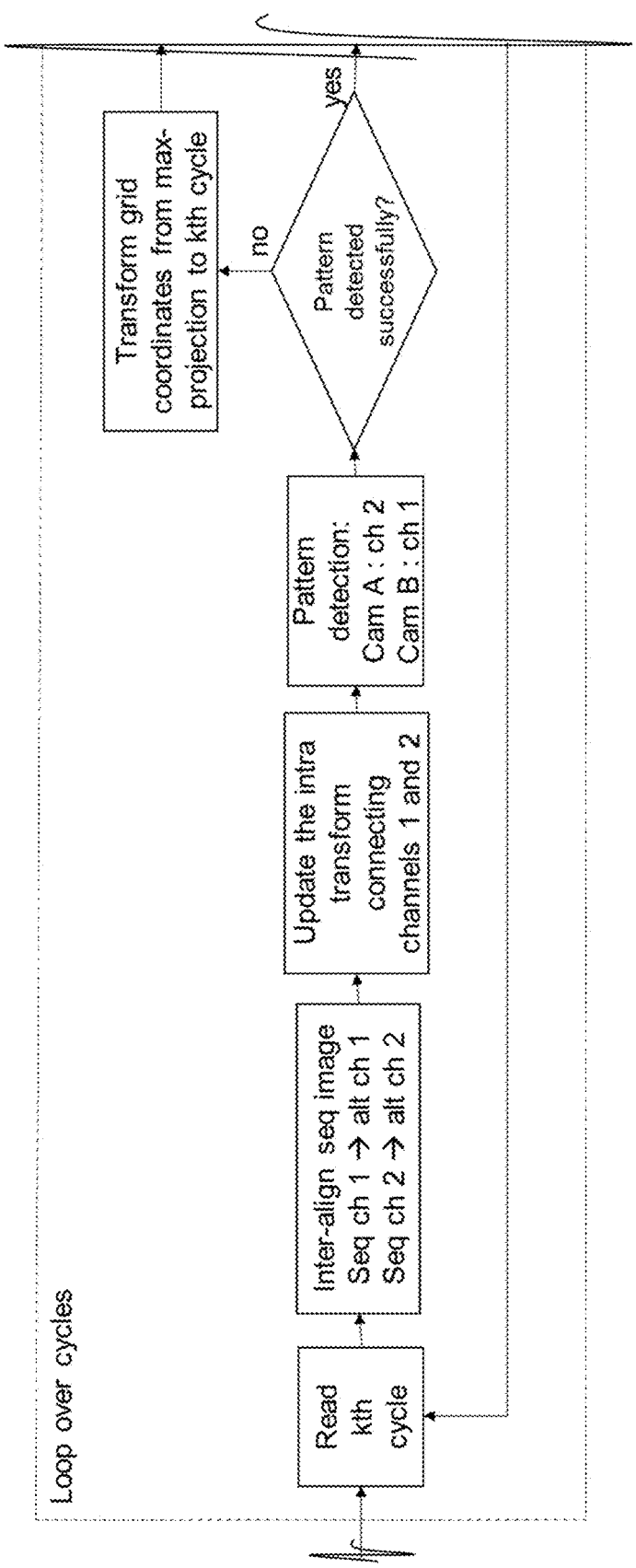
Figure 1D:
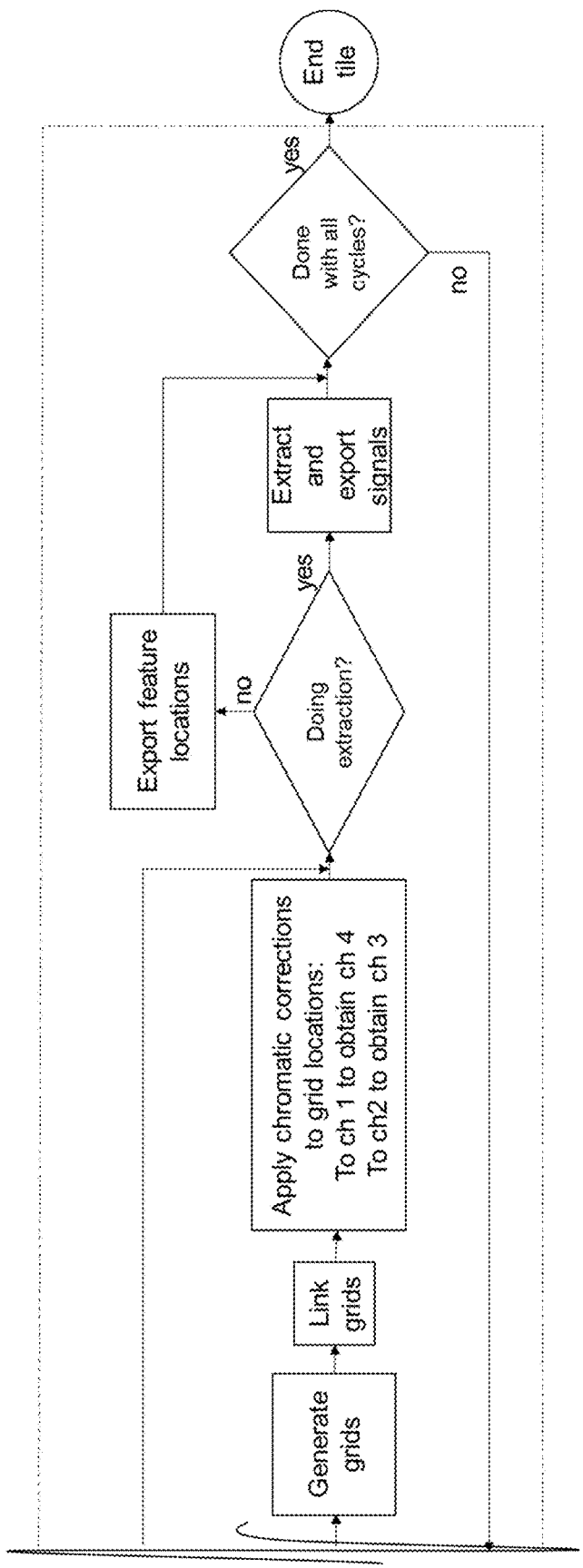

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, N.Y. 1994); and Sambrook and Green, Molecular Cloning: A Laboratory Manual, 4th Edition (2012). Methods, devices and materials similar or equivalent to those described herein can be used in the practice of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise.

Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are "tethered", "coated", "attached", or "immobilized" to one another or to a common solid or semisolid support. An association may refer to covalent or non-covalent means for attaching labels to solid or semi-solid supports such as beads. In embodiments, primers on or bound to a solid support are covalently attached to the solid support. An association may comprise hybridization between a target and a label.

As used herein, the term "hybridize" or "specifically hybridize" refers to a process where two complementary nucleic acid strands anneal to each other under appropriately stringent conditions. Hybridizations are typically and preferably conducted with oligonucleotides. The terms "annealing" and "hybridization" are used interchangeably to mean the formation of a stable duplex. Non-limiting examples of nucleic acid hybridization techniques are described in, for example, Sambrook, et al., Molecular Cloning: A Laboratory Manual (2nd Edition, 1989).

As used herein, the term "nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

As used herein, the terms "polynucleotide primer" and "primer" refers to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both.

As used herein, the term "label" or "labels" generally refer to molecules that can directly or indirectly produce or result in a detectable signal either by themselves or upon interaction with another molecule. Non-limiting examples of detectable labels include labels comprising fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.).

As used herein, the terms "solid support" and "substrate" and "solid surface" refers to discrete solid or semi-solid surfaces to which a plurality of primers may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A solid support may be used interchangeably with the term "bead." A solid support may further comprise a polymer or hydrogel on the surface to which the primers are attached. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. Useful substrates include those that allow optical detection, for example, by being translucent to energy of a desired detection wavelength and/or do not produce appreciable background fluorescence at a particular detection wavelength. The solid supports for some embodiments have at least one surface located within a flow cell. The solid support, or regions thereof, can be substantially flat. The solid support can have surface features such as wells, pits, channels, ridges, raised regions, pegs, posts or the like. The term solid support is encompassing of a substrate (e.g., a flow cell) having a surface comprising a polymer coating covalently attached thereto. In embodiments, the solid support is a flow cell. The term "flowcell" as used herein refers to a chamber including a solid surface across which one or more fluid reagents can be flowed. Examples of flowcells and related fluidic systems and detection platforms that can be readily used in the methods of the present disclosure are described, for example, in Bentley et al., Nature 456:53-59 (2008).

The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/$cm^2$, at least about 1,000 features/$cm^2$, at least about 10,000 features/$cm^2$, at least about 100,000 features/$cm^2$, at least about 10,000,000 features/$cm^2$, at least about 100,000,000 features/$cm^2$, at least about 1,000,000,000 features/$cm^2$, at least about 2,000,000,000 features/$cm^2$ or higher. In embodiments, the arrays have features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher. In embodiments, the array is provided in a microplate. The term "microplate", as used herein, refers to a substrate comprising a surface, the surface including a plurality of reaction chambers separated from each other by interstitial regions on the surface. In embodiments, the microplate has dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The dimensions of the microplate as described herein and the arrangement of the reaction chambers may be compatible with an established format for automated laboratory equipment. The reaction chambers may be provided as wells (alternatively referred to as reaction chambers), for example a microplate may contain 6, 12, 24, 48, 96, 384, or 1536 sample wells arranged in a 2:3 rectangular matrix. In embodiments, the reaction chamber is a microscope slide (e.g., a glass slide about 75 mm by about 25 mm). In embodiments the slide is a concavity slide (e.g., the slide includes a depression). In embodiments, the slide includes a coating for enhanced cell adhesion (e.g., poly-L-lysine, silanes, carbon nanotubes, polymers, epoxy resins, or gold). In embodiments, the microplate is about 5 inches by 3.33 inches, and includes a plurality of 5 mm diameter wells. In embodiments, the microplate is a flat glass or plastic tray in which an array of wells are formed, wherein each well can hold between from a few microliters to hundreds of microliters of fluid reagents and samples. The term "well" refers to a discrete concave feature in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular. The wells of a microplate are available in different shapes, for example F-Bottom: flat bottom; C-Bottom: bottom with minimal rounded edges; V-Bottom: V-shaped bottom; or U-Bottom: U-shaped bottom. In embodiments, the well is square.

As used herein, the terms "cluster" and "colony" are used interchangeably to refer to a discrete site on a solid support that includes a plurality of immobilized polynucleotides and a plurality of immobilized complementary polynucleotides. The term "clustered array" refers to an array formed from such clusters or colonies. In this context the term "array" is not to be understood as requiring an ordered arrangement of clusters.

As used herein, the term "selective" or "selectivity" or the like of a compound refers to the compound's ability to discriminate between molecular targets.

The terms "bind" and "bound" as used herein are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules (e.g., as in a substrate, bound to a first antibody, bound to an analyte, bound to a second antibody), thereby forming a complex. As used herein, the term "attached" refers to the state of two things being joined, fastened, adhered, connected or bound to each other. For example, a nucleic acid, can be attached to a material, such as a hydrogel, polymer, or solid support, by a covalent or non-covalent bond. In embodiments, attachment is a covalent attachment.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

The terms "sequencing", "sequence determination", "determining a nucleotide sequence", and the like include determination of partial as well as full sequence information of the polynucleotide being sequenced. That is, the term includes sequence comparisons, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. As used herein, the term "sequencing cycle" is used in accordance with its plain and ordinary meaning and refers to incorporating one or more nucleotides to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

As used herein, the term "feature" refers a point or area in a pattern that can be distinguished from other points or areas according to its relative location. An individual feature can include one or more polynucleotides. For example, a feature can include a single target nucleic acid molecule having a particular sequence or a feature can include several nucleic acid molecules having the same sequence (and/or complementary sequence, thereof). Different molecules that are at different features of a pattern can be differentiated from each other according to the locations of the features in the pattern. Non-limiting examples of features include wells in a substrate, particles (e.g., beads) in or on a substrate, polymers in or on a substrate, projections from a substrate, ridges on a substrate, or channels in a substrate. In embodiments, a feature refers to a location in an array where a particular species of molecule is present. A feature can contain only a single molecule or it can contain a population of several molecules of the same species. Features of an array are typically discrete. The discrete features can be contiguous or they can have spaces between each other. The size of the features and/or spacing between the features can vary such that arrays can be high density, medium density or lower density. High density arrays are characterized as having sites separated by less than about 15 µm (e.g., 3-6 µm). Medium density arrays have sites separated by about 15 to 30 µm. Low density arrays have sites separated by greater than 30 µm. An array useful herein can have, for example, sites that are separated by less than 10 µm, 5 µm, 1 µm, or 0.5 µm. An apparatus or method of the present disclosure can be used to detect an array at a resolution sufficient to distinguish sites at the above densities or density ranges.

In embodiments, the features have a mean or median separation from one another of about 0.5-5 µm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 µm or a number or a range between any two of these values. In embodiments, the mean or median separation is about 0.1-10 microns. In embodiments, the mean or median separation is about 0.25-5 microns. In embodiments, the mean or median separation is about 0.5-2 microns.

In embodiments, the features have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about or at most about 100, 200, 300, 400, 500, 600, 700, 800, 900, 1000, 1100, 1200, 1300, 1400, 1500, 1600, 1700, 1800, 1900, 2000 nanometers or a number or a range between any two of these values.

The distances between features can be described in any number of ways. In some embodiments, the distances between features can be described from the center of one feature to the center of another feature. In other embodiments, the distances can be described from the edge of one feature to the edge of another feature, or between the outer-most identifiable points of each feature. The edge of a feature can be described as the theoretical or actual physical boundary on a chip, or some point inside the boundary of the feature. In other embodiments, the distances can be described in relation to a fixed point on the object or in the image of the object.

The term "pitch," is used in accordance with its ordinary meaning when used in reference to features of an array, and refers to the spacing (e.g., center-to-center) for adjacent features. The term refers to spacing in the xy dimension. A pattern of features can be characterized in terms of average pitch. The pattern can be ordered such that the coefficient of variation around the average pitch is small or the pattern can be random in which case the coefficient of variation can be relatively large. In either case, the average pitch can be, for example, at least about 10 nm, about 0.1 µm, about 0.5 µm, about 1 µm, about 5 µm, about 10 µm, or more. In embodiments, the average pitch can be, about 10 µm, about 5 µm, about 1 µm, about 0.5 µm, about 0.1 µm or less. In embodiments, features are 450 nm in diameter with a pitch of 1.4 µm.

The term "image" is used according to its ordinary meaning and refers to a representation of all or part of an object. The representation may be an optically detected reproduction. For example, an image can be obtained from a detection apparatus configured to obtain fluorescent, luminescent, scatter, or absorption signals. The part of the object that is present in an image can be the surface or other xy plane of the object. Typically, an image is a 2 dimensional representation of a 3 dimensional object. An image may include signals at differing intensities (i.e., signal levels). An image can be provided in a computer readable format or medium.

As used herein, the term "signal" is intended to include, for example, fluorescent, luminescent, scatter, or absorption impulse or electromagnetic wave transmitted or received. Signals can be detected in the ultraviolet (UV) range (about 200 to 390 nm), visible (VIS) range (about 391 to 770 nm), infrared (IR) range (about 0.771 to 25 microns), or other range of the electromagnetic spectrum. The term "signal level" refers to an amount or quantity of detected energy or coded information. For example, a signal may be quantified by its intensity, wavelength, energy, frequency, power, luminance, or a combination thereof. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

The term "xy coordinates" refers to information that specifies location, size, shape, and/or orientation in an xy plane. The information can be, for example, numerical coordinates in a Cartesian system. The coordinates can be provided relative to one or both of the x and y axes or can be provided relative to another location in the xy plane (e.g., a fiducial). The term "xy plane" refers to a 2 dimensional area defined by straight line axes x and y. When used in reference to a detecting apparatus and an object observed by the detector, the xy plane may be specified as being orthogonal to the direction of observation between the detector and object being detected.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques. SBS techniques generally involve the enzymatic extension of a nascent nucleic acid strand through the iterative addition of nucleotides against a template strand. SBS techniques can utilize nucleotides that have a label moiety or those that lack a label moiety. Accordingly, incorporation events can be detected based on a characteristic of the label, such as fluorescence of the label. In embodiments, where two or more different nucleotides are present in a sequencing reagent, the different nucleotides can be distinguishable from each other, or alternatively, the two or more different labels can be the indistinguishable under the detection techniques being used.

Image analysis algorithms or processes useful for extracting signals from randomly located points, such as fluorescent beads, generally include two steps: i) detecting the point locations, and ii) extracting the fluorescent intensities from those point locations. For example, a first feature may be detected at $(x_1, y_1, z_1)$ with a fluorescent intensity at that position, $I_1(x_1, y_1, z_1)$, while a second feature is detected at $(x_2, y_2, z_2)$ having fluorescent intensity, $I_2(x_2, y_2, z_2)$. This feature extraction typically works well under low density conditions, i.e., when there is significant distance between neighboring points. However, neither of the two steps account for the proximity of neighboring features. As the density of points of the image increases, the accuracy of such algorithms can degrade due to the spatial overlap of images. Such degradation tends to cause errors in both steps of the aforementioned algorithm.

Approaches to account for and potentially correct errors caused by overlapping images include introducing a point spread function (PSF), which serves to deconvolute the feature before the detection of the feature. The overlapping images and subsequent overlapping PSFs, can act to couple the location and intensities of the feature allowing for a joint solution for these quantities in each local neighborhood of the image. This can be done by, for example, minimizing the squared error between the image patch and its model over the space of candidate locations and intensities, where the model is constructed using an exemplar feature shape (e.g., a circle) and the PSF. However, this can significantly increase the computational load and may be more prone to introducing aberrations due to the technical complexity of implementing a PSF-corrected image.

A significant improvement is achieved by arranging otherwise random distribution of features onto an ordered array (i.e., a pattern). For example, with the features arranged on a regular grid, there is no need to detect individual feature locations since the locations (x, y, z) are fixed and known. Note, the ordered pattern or ordered array does not necessarily need to be rectilinear (e.g., an x-y format of features that are in rows and columns), so long as the feature pattern and corresponding interstitial regions is known. The feature pattern is then registered with respect to a pixel grid. The pattern registration is described by a small number of parameters or parameter data, such as the grid orientation angle, the apparent pitch in pixel units, and the phase of the feature grid at some fixed pixel location. These parameters are determined from an average over features, so that even if the signal-to-noise ratio of an individual feature is low, accurate sub-pixel registration is possible. By knowing the pattern registration, it is then a matter to calculate the locations of all features, such that the only the intensities need to be determined, thereby reducing the number of variables threefold.

The feature extraction analysis begins by building a model of the image incorporating the known feature locations and their unknown intensities and fitting the model to the actual image. This may result in generation of image-related data. The model of image formation is described by the linear system Bc=y, where c is the unknown vector of feature intensities, y is a column vector of all pixel intensities (the image flattened into 1D), and B is a matrix of size $(N_{pixels}, N_{features})$. Each row of B corresponds to a pixel and describes the contribution of each feature to that pixel. B is constructed using the knowledge of the feature locations, their model shape and the PSF. B is a very sparse matrix, because fluorescence from one feature only reaches a few pixels, or conversely, a pixel only sees significant contributions from perhaps seven nearest features at most. This is an overdetermined system, since there are more pixels than features, and allows for a least-squares fit solution.

As a sequencing run progresses, multiple images of the pattern with the same parameters (e.g., pitch, orientation angle, etc.) are taken over and over. The feature intensities and pixel intensities vary cycle-to-cycle (i.e., the feature and pixel intensities vary each sequencing cycle), but the underlying pattern is immutable. Therefore, only a relatively small number of matrices B is sufficient to describe image formation for a much larger total number of images from a run, or a plurality of runs. This permits realization of large computation time savings by reusing the matrices. Some or all versions of B describing the pattern and its possible phasing may be pre-computed, inverted, and stored in a database, indexed by the pattern parameters. When performing signal extraction on a particular image y, an appropriate inverse matrix, $B^+$ is formulated and used to extract the feature intensities via sparse matrix multiplication:

$c=B^+y.$

In embodiments, the matrices B+ are not used directly to the images. Instead, they are used to construct a bank of convolution filters. The filters, when applied to the images, produce equivalent results to the matrix multiplication described above. Significant memory and compute savings are realized, while preserving sub-pixel accuracy. Another benefit is code simplification.

The pattern may be a regular hexagonal grid with known nominal pitch and orientation angle. The pattern pitch and angle may have deviations from the nominal; e.g., <2% deviation is expected for the pitch to account for the variability in the imaging optics magnification. The pattern pitch and angle may also vary across the image due to the distortion of the optics. For example, less than about 1% distortion is expected. In embodiments, the pattern is ordered in a lattice, e.g., a hexagonal lattice or Bravais lattice. In embodiments, the pattern is ordered in a cubic, hexagonal, rhombohedral, tetragonal, orthorhombic, monoclinic, or a triclinic lattice. Alternatively, in embodiments, the pattern may be a random pattern (i.e., a non-hexagonal grid). Note, the ordered pattern or ordered array (e.g., an ordered lattice) does not necessarily need to be rectilinear (e.g., an x-y format of features that are in rows and columns), so long as the feature pattern and corresponding interstitial regions is known.

In embodiments, fluorescent features are assumed to be located on the hexagonal grid and are assumed to be similar in size and shape.

In embodiments, the image does not contain a focusing bead. In embodiments, the image includes a focusing bead. Focusing beads are high brightness features that are similar in size to the sequencing features. Focusing beads may adhere to the same grid pattern as the sequencing features. Alternatively, the focusing beads may be randomly placed.

In embodiments, each image contains one or more fiducials that serve as the origin for indexing of the features and tracking them cycle-to-cycle (i.e., tracking them every sequencing cycle). The term "fiducial" is intended to mean a distinguishable point of reference in or on an object. The point of reference can be, for example, a mark, second object, shape, edge, area, irregularity, channel, pit, post or the like. The point of reference can be present in an image of the object or in another data set derived from detecting the object. The point of reference can be specified by an x and/or y coordinate in a plane of the object. Alternatively, the point of reference can be specified by a z coordinate that is orthogonal to the xy plane, for example, being defined by the relative locations of the object and a detector.

The image analysis may use the following inputs, which are non-limiting examples: a set of four-channel (i.e., four-color) images corresponding to sequencing cycles of one tile; a four-channel image of focusing beads (if present); a configuration file describing the pattern parameters (e.g., nominal pitch and orientation of the pattern, the pixel pitch, etc.); and optionally, a file of pre-computed extraction matrices. In embodiments, the image analysis includes a set of four-channel (i.e., four-color) images corresponding to sequencing cycles of one tile as an input. In embodiments, the image analysis includes a four-channel image of focusing beads (if present) as an input. In embodiments, the image analysis includes a configuration file describing the pattern parameters (e.g., nominal pitch and orientation of the pattern, the pixel pitch, etc.) as an input. In embodiments, the image analysis includes a file of pre-computed extraction matrices as an input. The image analysis process can output, for example, a single file (e.g., an HDF5 file) per cycle listing for every feature detected, including feature center coordinates in image pixels; a feature index; extracted signal levels (i.e., intensity values); and a single file per cycle with extracted intensities. The image analysis process can output, for example, a one or more files in a suitable format that includes information for every feature detected, including feature center coordinates in image pixels; a feature index; extracted signal levels (i.e., intensity values). In embodiments, the image analysis process provides a single electronic computer-readable data file per cycle with extracted intensities.

EXAMPLES

A general overview of an example workflow or method is provided in FIGS. 1A-1D. The workflow uses an initial configuration file, which specifies the parameters of the expected pattern, such as the expected pitch and orientation angle. It also specifies the internal code parameters such as the size of the sub-images and their overlap regions.

Focusing beads may be located randomly, i.e., not adhering to the pattern grid, and may therefore be a source of noise for the pattern detection algorithm. Occasionally, the focusing beads are brighter than cluster. In order to improve the signal-to-noise ratio (SNR) of the pattern, the focusing bead images are altered before running pattern detection. The focusing beads detected in the altered image (referred to as an alt image), and a binary map of their location is stored. For each of the sequencing images, the map is aligned to the image, and the pixels belonging to the focusing beads are "in-painted", i.e. focusing beads are erased and their pixels are filled with values interpolated from their immediate surroundings.

Figure 2A:
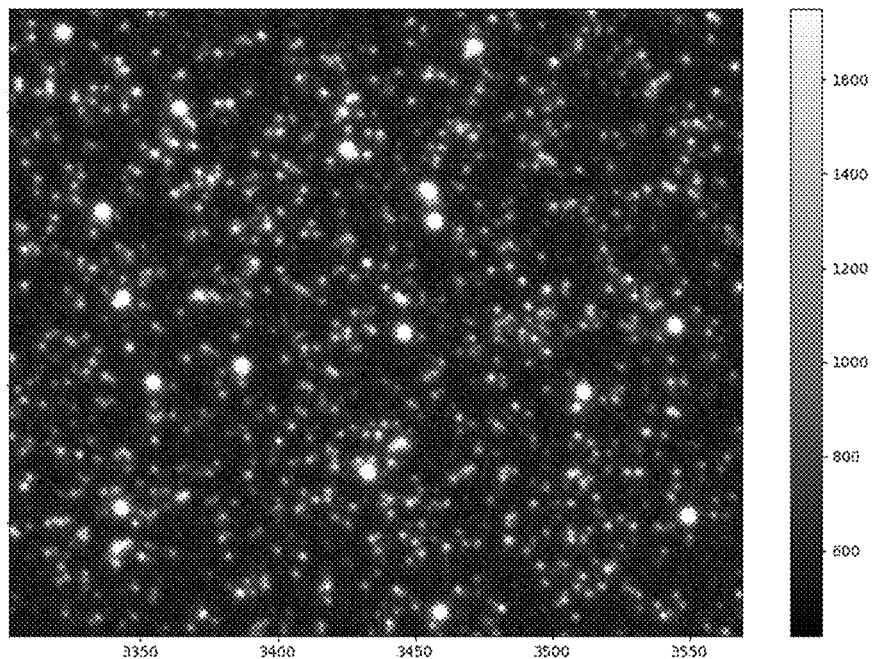
FIG. 2A and FIG. 2B show the same fragment of a single channel image, with about 16 focusing beads visible among sequencing clusters. In non-limiting examples, the focusing beads' typical peak intensity is 10,000 counts, which are the bright circles in FIG. 2A.
Figure 2B:
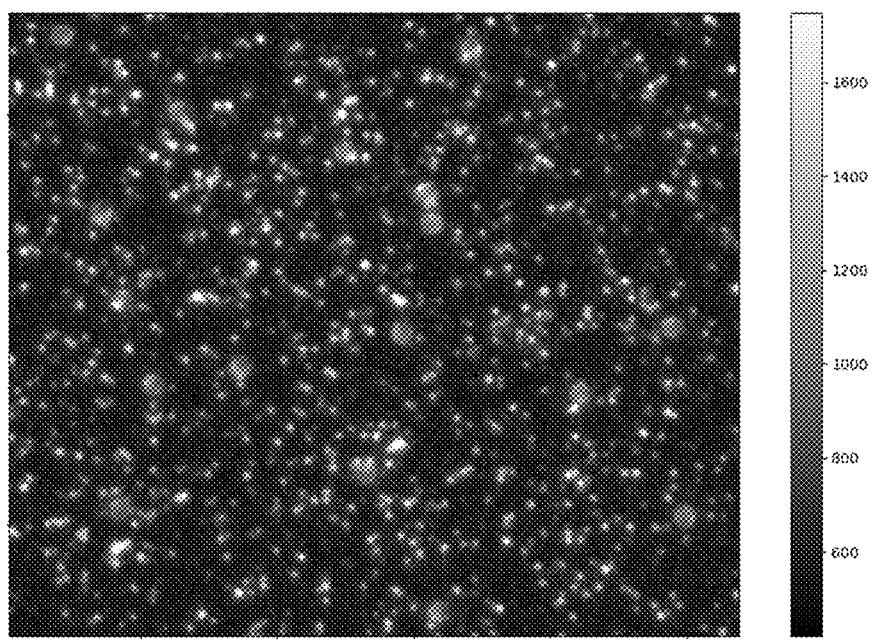

Both FIG. 2A and FIG. 2B show the same fragment of a single channel image, with about 16 focusing beads visible among sequencing clusters. The focusing beads' typical peak intensity is 10,000 counts, which are the bright circles in FIG. 2A. FIG. 2B shows the focusing beads flattened by the inpainting routine, wherein the intensity of the focusing beads are decreased to within about 1600 counts.

Chromatic aberration correction. In an example embodiment, a sequencing instrument has a detection apparatus that can include at least two cameras (referred to herein as camera A and camera B), each capable of imaging two different color channels, for example, coinciding with different labels used to distinguish one nucleotide base type from another are particularly applicable. Camera A collects images of fluorescent channels 2 and 3, and camera B collects channels 1 and 4. Channels that are imaged by the same cameras have different spectral wavelengths, and the optics have some lateral chromatic aberration. As a result of that, a chromatic correction is performed in order to associate the feature images in the channels of the same camera, e.g. 1 and 4 of camera B. The effect is particularly large, on the order of 1 pixel, for camera B, whose two channels are at the extreme ends of the fluorescence spectrum. The correction takes the form of a coordinate transform. An affine transform, i.e. a linear transform allowing for rotation, scale, shear and translation, was found to adequately describe the chromatic shift between channels of the same camera. The transform is different for different instances of the instrumental hardware. The transform is calculated automatically from the maximum intensity projection (max-projection) of the sequencing images of the first few (such as 5-20) cycles. The max-projection is constructed based on the sequencing images warped such that channel 1 aligns to the channel 1 of the alt image, and channel 2 aligns to the channel 2 of the alt image. The same warp applied to channel 4 as that for channel 1, which is on the same camera. Likewise the warp of channel 2 is applied to channel 3. With the images warped in this way, the max projection is built up for each of the four channels. The channel 4 of the max projection is then aligned to the channel 1 of the max projection to obtain the chromatic correction affine transform for camera B. Likewise the channel 3 of the max projection is then aligned to the channel 2 to obtain the chromatic correction affine transform for camera A. A direct (as opposed to feature-based) image alignment method is used to find the affine transform. Concretely, FindTransformECC from the OpenCV library with the affine motion model is applied to the entire image, with the exception of a small border region. The intra-camera chromatic shifts are assumed to be stable over the course of the run. They are stored and used for coordinate transforms in subsequent processing.

Figure 3:
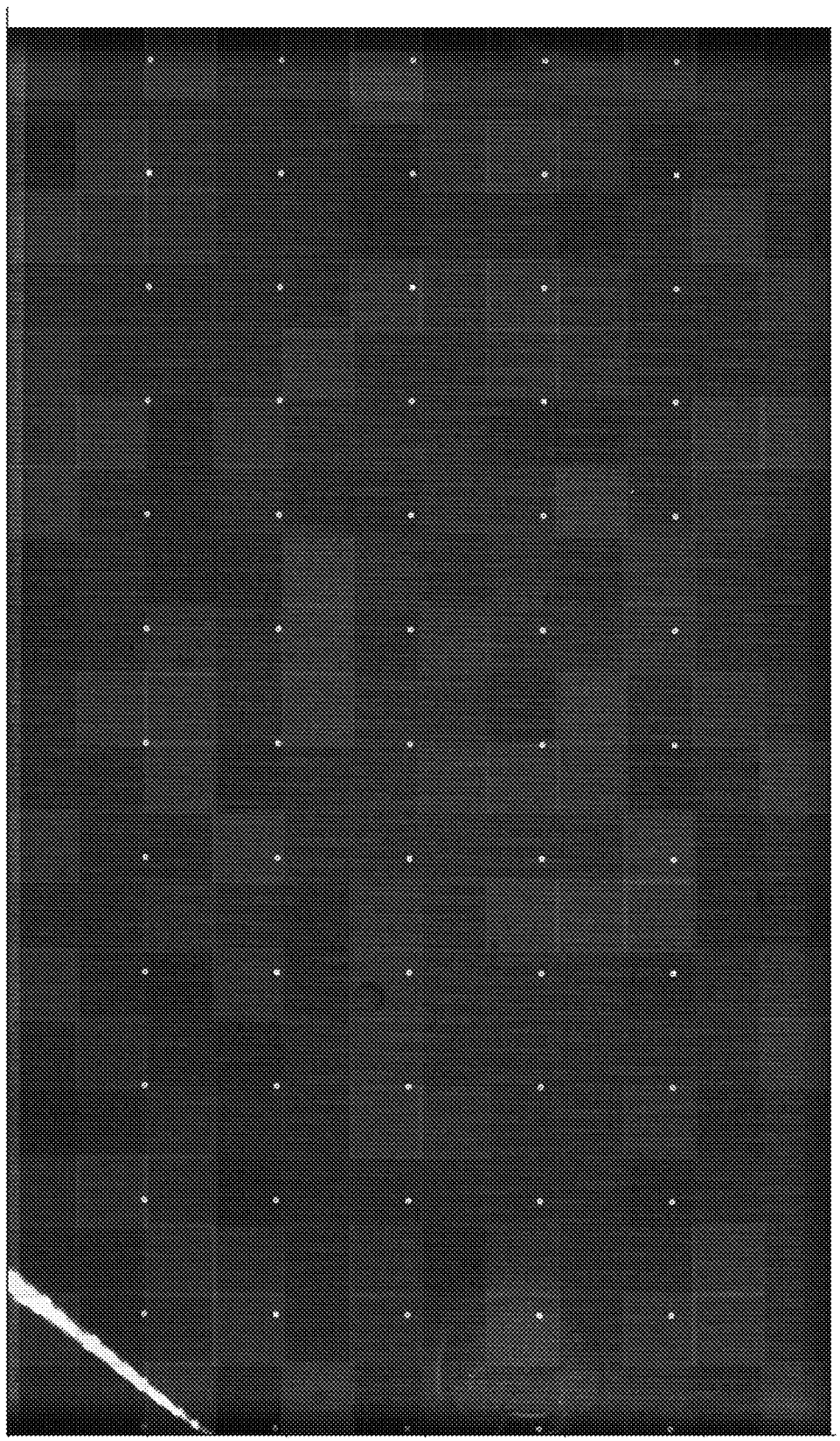
FIG. 3 shows an illustration of partitioning wherein each subimage, when present, is highlighted with a differently shaded box. The partitioning scheme can be independent of the image content and can be fully defined by a subimage size and overlap defined in an input configuration file.

Partition of the image for pattern registration purposes. The image is partitioned into overlapping square subimages, for example as depicted in FIG. 3. In this example the subimages were 256×256 pixels with 8 pixel overlap. Subimages of 384×384 pixels with 224 pixel overlaps have also been used. Desired specifications for the partitioning scheme include:
 i) subimage spacing dense enough to capture apparent pitch variations due to lens distortion; and
 ii) large enough overlaps and dense enough spacing to provide redundancy in case pattern detection fails in some subimages One reason for the partitioning is the geometrical distortion of the image by the optics. The imaging optics of the sequencer have a small but significant barrel distortion of −0.5%, resulting in about 1% difference in apparent pitch between the central and corner portions of the image. Not taking this into account would result in an error of locating features equivalent to several feature pitches. The lithographically made pattern of the FC features may also conceivably deviate from perfectly uniform dimensions, in which case the partitioning scheme would also take that non-uniformity into account.

Figure 4A:
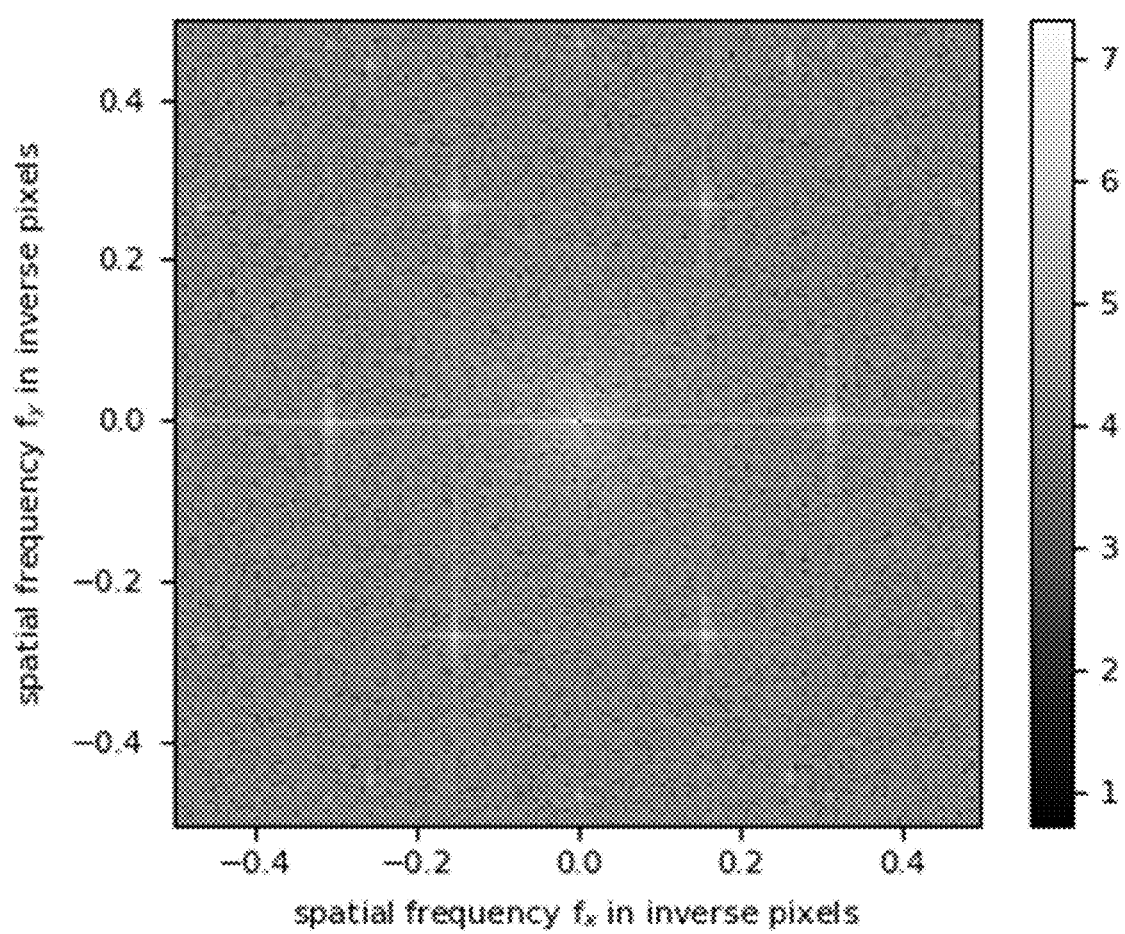
FIG. 4A shows an example of a 2D discrete Fourier transform (DFT), which is computed for each subimage. The absolute value of the complex-valued transform is shown as an image on a log scale. The zero of the spatial frequency is in the center of the plot in FIG. 4.

Local pattern registration. The pattern parameters are assumed constant within each subimage. For each subimage, a 2D discrete Fourier transform (2D DFT) is computed. The absolute value of the complex-valued transform is shown in FIG. 4 as an image on a log scale. The zero of the spatial frequency is in the center of the plot.

When a hexagonal pattern is present in the original subimage, 3 pairs of peaks are found in the DFT amplitude. The integer locations of the peaks are found by local search for max signal in the neighborhoods that are predicted by the nominal pattern pitch and orientation config parameters. The locations of the amplitude peaks are further refined to sub-integer precision by the frequency estimation method of Quinn, B. G. (1994). "Estimating Frequency by Interpolation using Fourier Coefficients." IEEE Transactions on Signal Processing, 42(5), 1264-1268. The phase of the transform at the float frequencies is then estimated using the method of Robert G. Lyons, John D. Lord, "Estimating synchronization signal phase," Proc. SPIE 9409, 2015. The result of these are the three 2 d frequency vectors, and three scalar phase values.

After processing each subimage according to the transformations described above, the output of the pattern registration contains the three frequency vectors. The frequencies are expressed in inverse pixels The output also contains the phases, the boundaries of the subimage, and the x,y coordinates for each pattern feature locations.

Two equivalent descriptions of the hexagonal grid are used throughout the code. 1) Three vectors of spatial frequencies ($f_y$, $f_x$). 2) Three primitive vectors. The primitive vectors are vectors in pixel space that connect the nearest neighbor features to each other, i.e. the length of the vectors is the apparent pattern pitch, in pixel units. Functions are provided to convert between these representations. FIG. 4B illustrates the terminology and the relationships between the primitive vectors in image space and frequency vectors in the reciprocal space, aka Fourier space or frequency space.

Refining the pattern registration. Occasionally, the local pattern registration may fail for some subimages, or produce results that are inconsistent between neighboring subimages. This happens where there are few bright grid features, for example when the subimage is on the boundary of the illuminated region, it is dominated by prominent non-grid features like the annular fiducial or randomly placed focusing beads.

Each subimage partially overlaps with up to 8 neighbors (or fewer if on the image boundary). The features located in the overlap regions participate in up to 4 regions and get multiple values for their coordinates. Successful pattern registration implies that those multiple coordinate values must agree, which in turn implies that the pattern phases in the overlap regions must agree. For every pair of overlapping subimages, the phases of the pattern are computed for the geometric center of the overlap region. If the phases derived from the two subimages agree to within a given tolerance (e.g., 0.03 of one feature period by default), the two registrations are deemed in agreement. If there is an inconsistency that has to be resolved, this occurs by revising the registration within one or both of the subimages. The pairwise relationships connect all of the subimages together, so the inconsistencies cannot be resolved by just considering each pair in isolation.

An undirected graph was constructed where every vertex represents a subimage, and edges are added between subimages that overlap. Each edge has a phase difference associated with it. The edges where the phase difference exceeds the tolerance were removed. This usually breaks the initially connected graph into several disjoint subgraphs, shown in different colors in FIG. 5. The largest connected subgraph is considered 'good' and the registration parameters of all the subimages/vertices that fall outside of the good graph were revised. Every subimage outside of the good graph conforms by setting its frequencies and phases to be the equal to the values interpolated from the neighbors that do belong to the good graph. Weighing the neighbors' contributions to the interpolation by their connectivity to the rest of the good graph.

Figure 5:
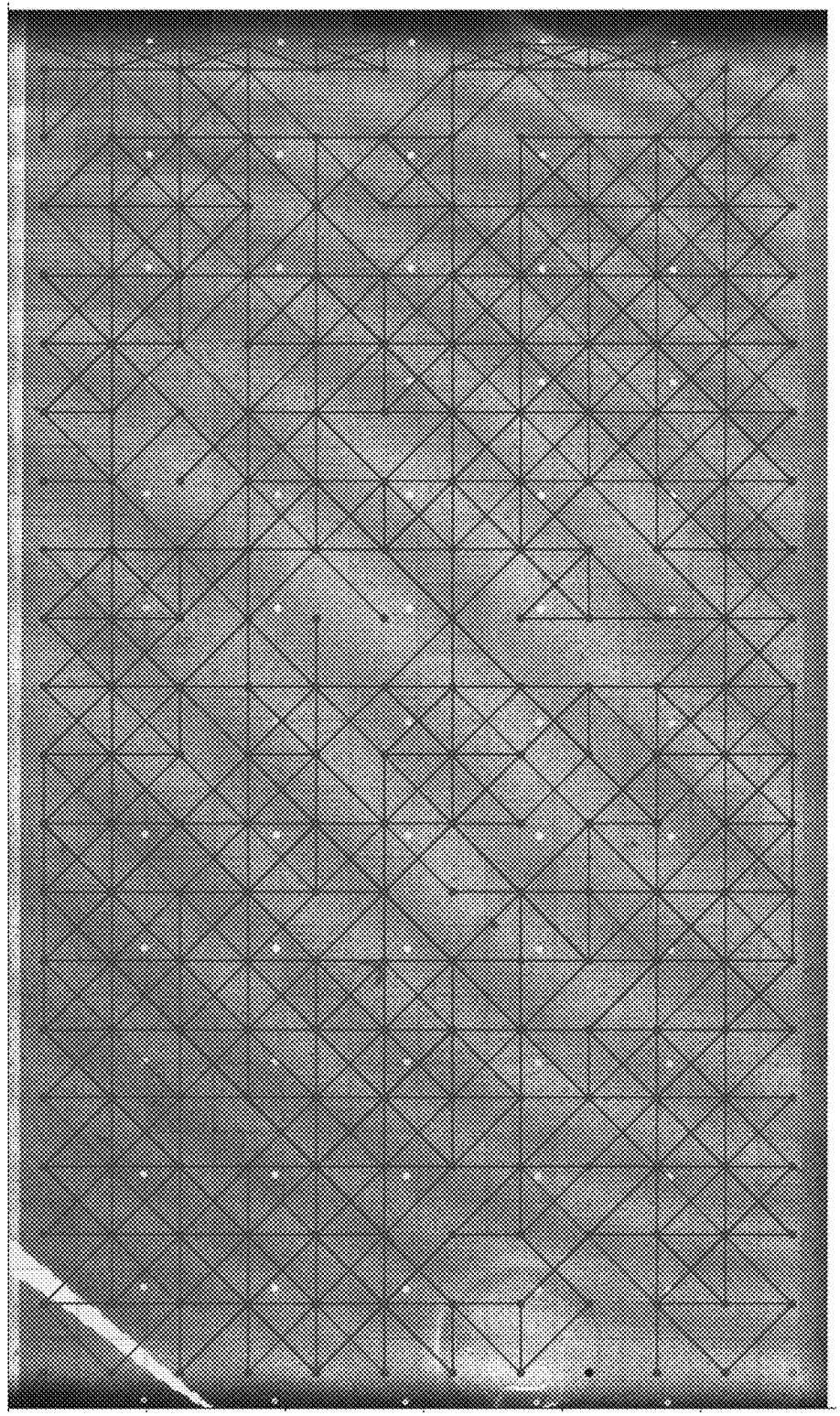
FIG. 5 shows an image of a pattern revealed by a fluorophore pattern probe. The pattern is overlaid with a graph representing results of pattern detection. The image of FIG. 5 shows that pattern estimates from almost all subimages agree with or correspond to each other.
Figure 6:
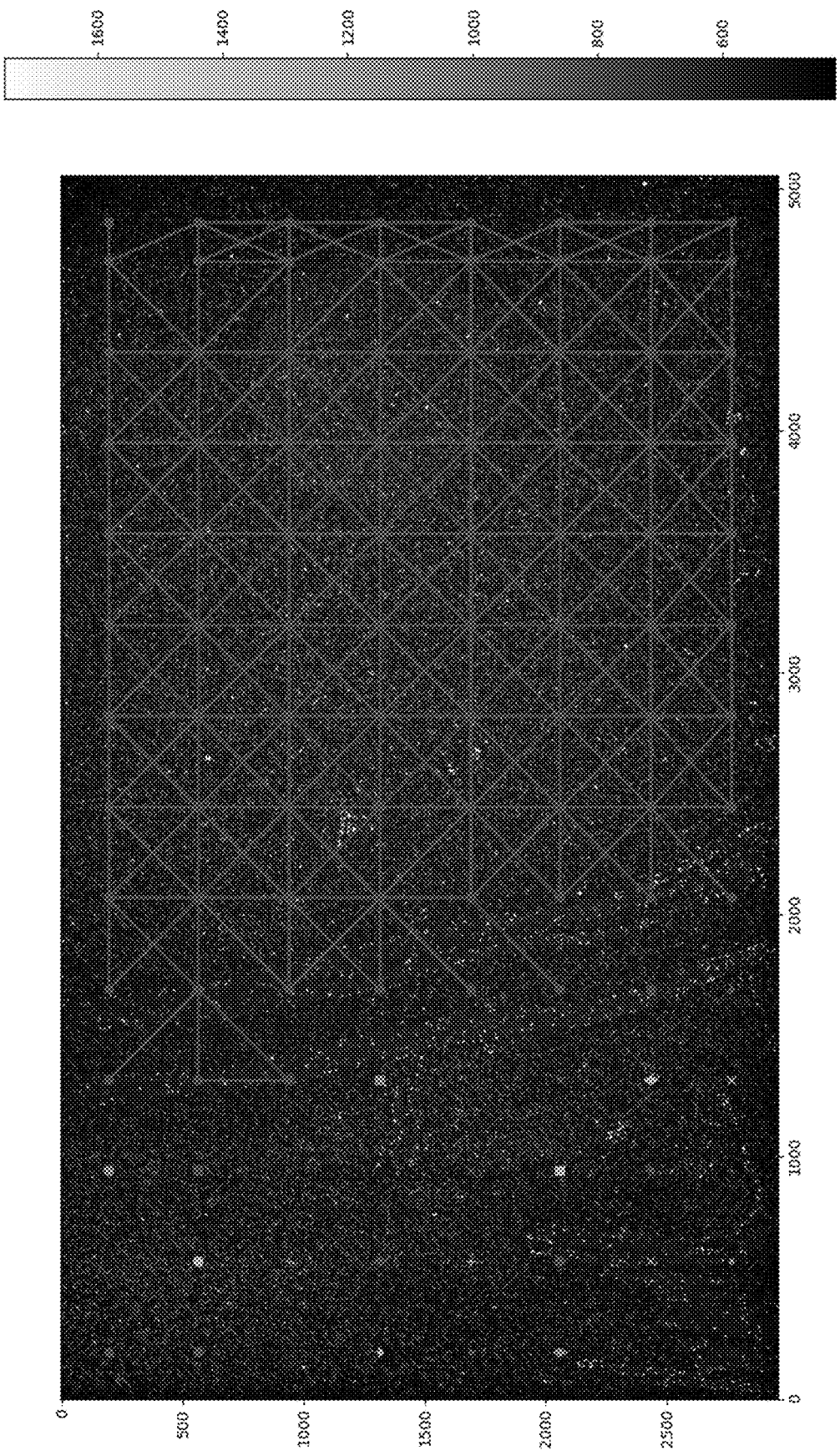
FIG. 6 shows a sequencing image from a single cycle, a single tile, and a single channel. The pattern registration produces pattern parameters that are consistent across a part of the image.

FIG. 5 shows an image of a pattern revealed by a fluorophore pattern probe. It is overlaid with the graph representing the results of pattern detection. It shows that pattern estimates from almost all subimages agree with each other. FIG. 6 shows a sequencing image from a single cycle, a single tile, and a single color channel. The pattern registration analysis produced pattern parameters that are consistent across a part of the image.

Generating local feature grids. After the spatial frequencies are computed for each subimage, two of the frequency vectors (out of three frequency vectors) are selected and are arranged into a 2×2 matrix. The matrix is inverted and transposed in order to compute the primitive vectors of the feature grid. These are the two pixel-space vectors that connect a feature to its immediate neighbors. Using the primitive vectors and phases, the pixel-space coordinates were computed for every feature in every subimage.

Figure 7A:
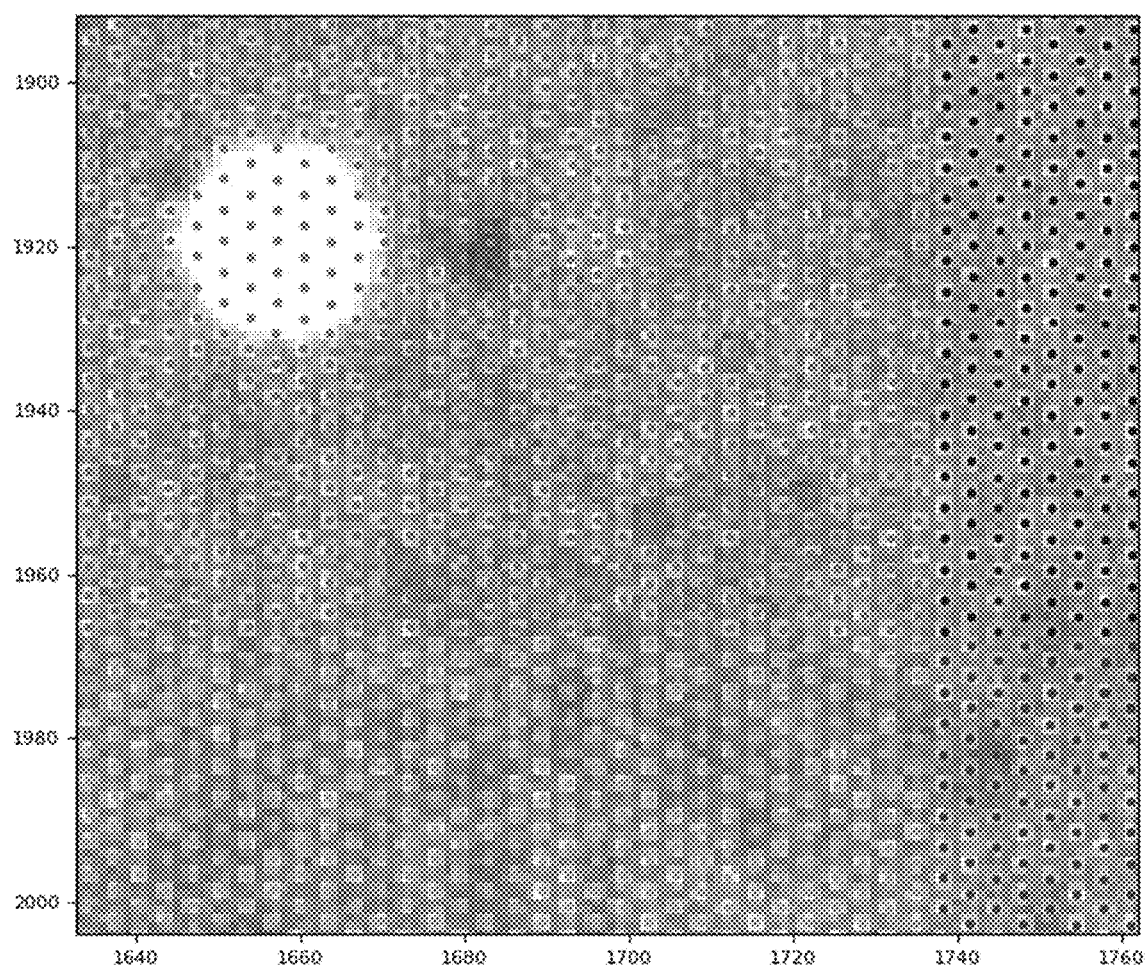
FIG. 7A shows a fragment of the image overlaid with the feature grid coordinates derived from the image via the local pattern registration procedure. The feature locations are shown as dots; the different shaded regions represent local grids computed from different subimages. Each feature further received a 2-component integer index (alternatively referred to herein as a "pair of integers" or "a 2-component integer vector" or "integer vector of length 2"), which can be stored in an exemplary field (e.g., a field called 'ij') in a computer.

The fragment of the image in FIG. 7A is overlaid with the feature grid coordinates derived from the image via the local pattern registration procedure. The registered feature locations are shown as dots; the different shaded regions represent local grids computed from different subimages. Each feature further received a 2-component integer index, stored in the field called 'ij'.

Linking of local patterns into a global feature map. This step re-bases the feature indices that come from all the different subimages so that they agree with each other. If a feature appears in an overlap region between two subimages, its two versions of the 'ij' index (alternatively referred to herein as a "pair of integers" or "a 2-component integer vector" or "integer vector of length 2") bear no relationship with each other, e.g. they may be (39,41) in one subimage and (0,1) in the neighbor. The routine traverses through the graph and for every subimage adds an offset to its feature indices to make them continuous. So, in the end the feature may have the index (1234, 567) in both subimages.

Fiducial detection. Each annular fiducial is located on the hexagonal grid, i.e., each fiducial is centered on a point where a feature would be if the fiducial were not there. There are several fiducials in every filed of view (FoV), spaced out by large enough distance (>>XY stage position error) so that their identity is unambiguous, i.e. one cannot mistake one particular fiducial for its respective neighbor.

A fiducial is detected by, for example, maximization of correlation with a template image or any of the classical feature detection techniques. The locations of fiducials on the mask are known, but can vary with respect to the instrument XY coordinate origin due to assembly variability and the variability of placement in the sequencing device. After a search over a large space in the first cycle images, the search space in subsequent cycles can be limited to be only slightly larger than the XY stage positioning accuracy, a few microns on the side, and so can be quite small.

If the pattern has previously been successfully detected, only one fiducial needs to be detected with high confidence. For example, when a fiducial is detected the identity is known from its approximate coordinates in the image and the stage position. The image coordinates are searched compared to the feature grid coordinates, and its 'ij' index (integer vector of length 2) is determined. The fiducial can then act as the origin (0,0) of the index of features. If multiple fiducials are detected, the multiple redundant detections may be used for quality control via consistency checking of their indices. Doing this for every cycle ensures that the same index (ij) refers to a unique feature on the flow cell throughout the run.

Background (glow) removal. The images typically contain diffuse background that slowly varies over the image. The background, or "glow" is different for each channel, and usually gradually increases with the cycle number. The background needs to be removed from the images prior to signal extraction.

The image is split into subimages. These subimages do not need to be the same as the subimages used for grid registration above. For example, 64×64 pixel subimages are used. All grid locations are known at this point. The image pixels where the grid feature centers fall are used for the background estimation. The idea is that a significant fraction of the grid sites are unoccupied, and so the pixel intensities at those sites represent the glow. The fraction is unknown in prior to extraction. The 5th percentile is used as the estimate of the glow for the subimage. Using the minimum (0th percentile) is faster, but may result in underestimation of the glow due to the presence of high-variance pixels in a typical camera sensor. Therefore, the background glow for each of the subimages is estimated as a single number. These estimates are interpolated using linear interpolation to create the glow estimate for every pixel in the image. This estimate is subtracted from the image before the extraction step.

The dimensions for the extraction matrix $B^+$ are ($N_{features}$, $N_{pixels}$) where $N_{pixels}$ is total number of pixels covered by the matrix.

Figure 7B:
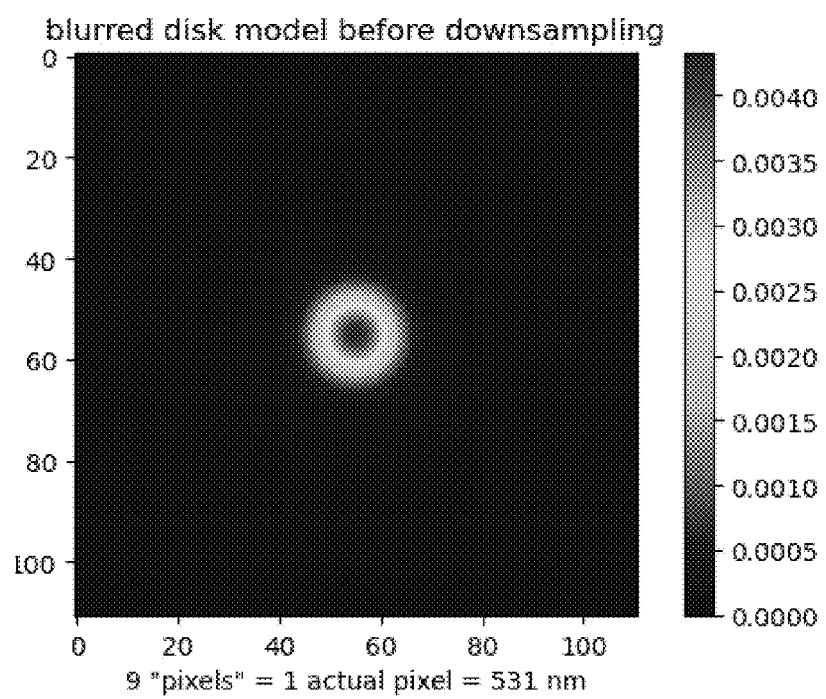
FIG. 7B shows an example of a synthetic model feature image.

Construction of the forward matrices. An initial function creates an oversampled model image of a single fluorescent feature. The feature is a disk given by the pattern design (e.g., a disk having a diameter of 0.7 microns), blurred by the PSF of the optics. The ideal disk image is convolved with the PSF (e.g., an Airy PSF, named after George Biddell Airy, or an experimentally measured PSF of the instrument). The synthetic image of the model disk is oversampled, i.e., the image has higher resolution than the real images, by a factor of 9 in each dimension. An example of the synthetic model feature image is shown in FIG. 7B.

Given the primitive vectors for the pattern and the $N_{pixels}=Q^2$ dimension of the matrix, the coordinates of all features that fall within the Q*Q pixels square are calculated. The result of this computation is a matrix of dimensions ($N_{features}$, 2) containing feature coordinates.

Figure 7C:
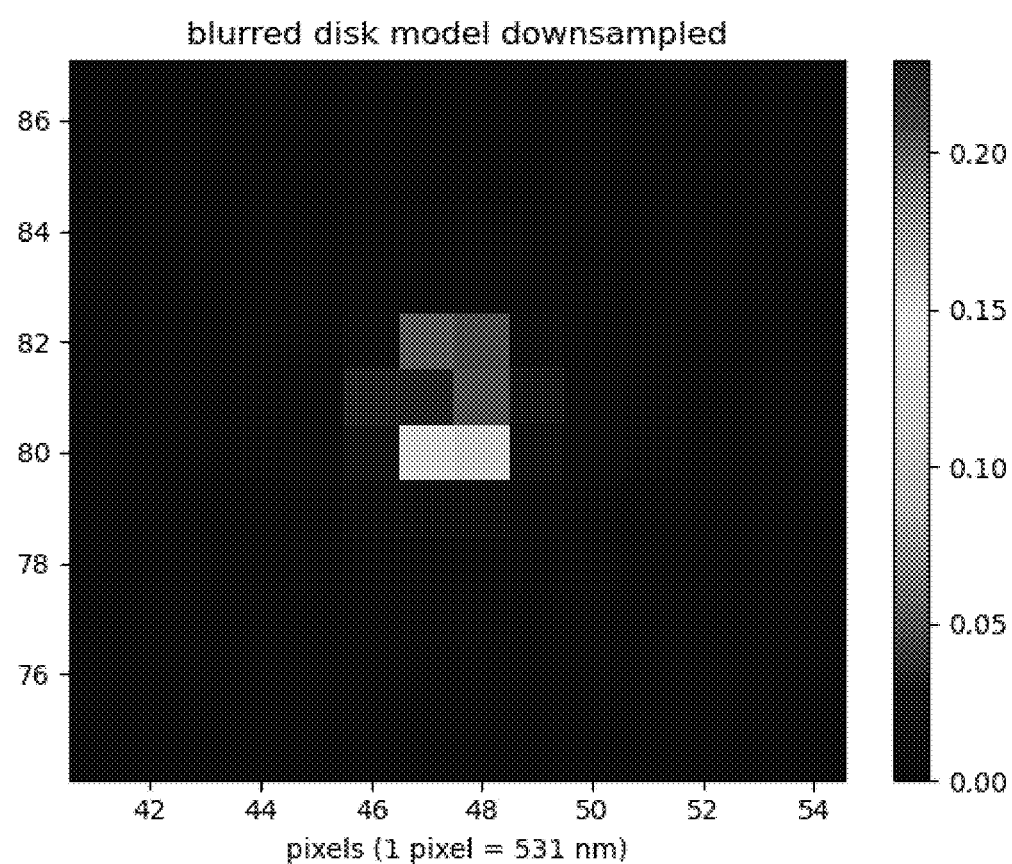
FIG. 7C shows an example of a blurred disk model downsampled to the pitch of the real pixels.

A 3D array of dimensions (Q, Q, $N_{features}$) is initialized to all zeros. For each feature n, the model disk image is written to the slice (:,:,n) of the 3 d array such that the disk is centered at the previously computed coordinates of the feature n. Because the disk image is oversampled, it is downsampled before being copied into its location such that it conforms to the pixel resolution of the destination array. Using the oversampled synthetic disk image, floating point feature coordinates, and downsampling the image appropriately ensures that resulting image is accurate to within a fraction of a pixel. Because the array contains only one feature per slice, it is extremely sparse (all but about 1% of values are zeros). The image in FIG. 7C shows an example of the blurred disk model downsampled to the pitch of the real pixels. It is asymmetric because in this case the coordinates of the center of the center do not fall on integer pixel coordinates, as is the general case. Downsampled disks vary in details of their shapes depending on the exact subpixel alignment of the center of the disk w.r.t. the pixel grid.

The 3D array is then reshaped in place to a 2D matrix, which we call the forward matrix B, whose dimensions are ($Q^2$,$N_{features}$), or, equivalently, ($N_{pixels}$, $N_{features}$). Each row of this matrix corresponds to a pixel, and each value in the row is the contribution of a feature to the value of the pixel. The matrix describes the image formation, transforming feature intensities into pixel intensities.

Figure 7D:
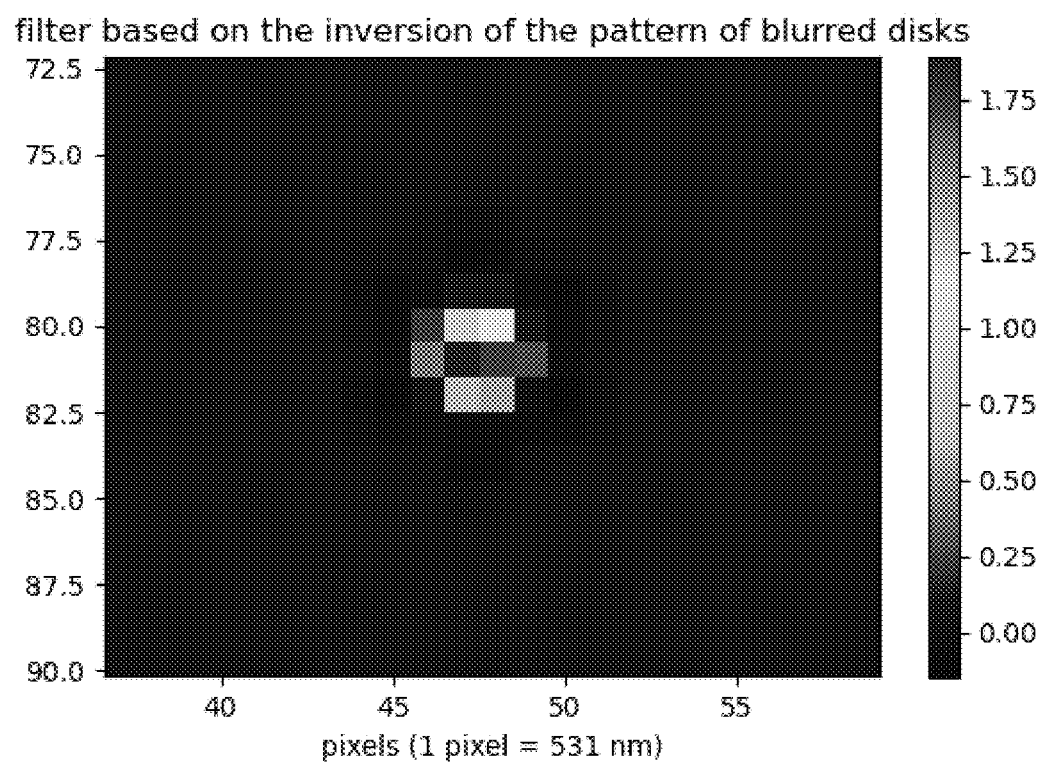
FIG. 7D shows an example of a portion of B+ corresponding to one particular feature n in the pattern.

Next, the matrix B is inverted to yield $B^+$. The Moore-Penrose pseudoinverse was used because the matrix is not square. The resulting inverse matrix $B^+$ with dimensions ($N_{features}$, $N_{pixels}$) is also very sparse, although less so than the forward matrix. Matrices that contain mostly zero values are considered sparse, distinct from matrices where most of the values are non-zero, called dense. It is computationally expensive to represent and work with sparse matrices as though they are dense, and much improvement in performance can be achieved by using representations and operations that specifically handle the matrix sparsity. The inverse matrix B+ with dimensions ($N_{features}$, $N_{pixels}$) is then reshaped to the tensor of dimensions ($N_{features}$, Q, Q). The image in FIG. 7D shows an example of a portion of B+ corresponding to one particular feature n in the pattern. The image is an excerpt from the slice B+(n, :, :). This can be thought of as a filter kernel that is multiplied together with a patch of the image to recover the total integrated intensity of a fluorescent feature. The kernel is of somewhat smaller but comparable full width at half maximum (FWHM) to the blurred disk model, and has negative-valued regions in locations where the neighboring features would be in the hex pattern.

Figure 7E:
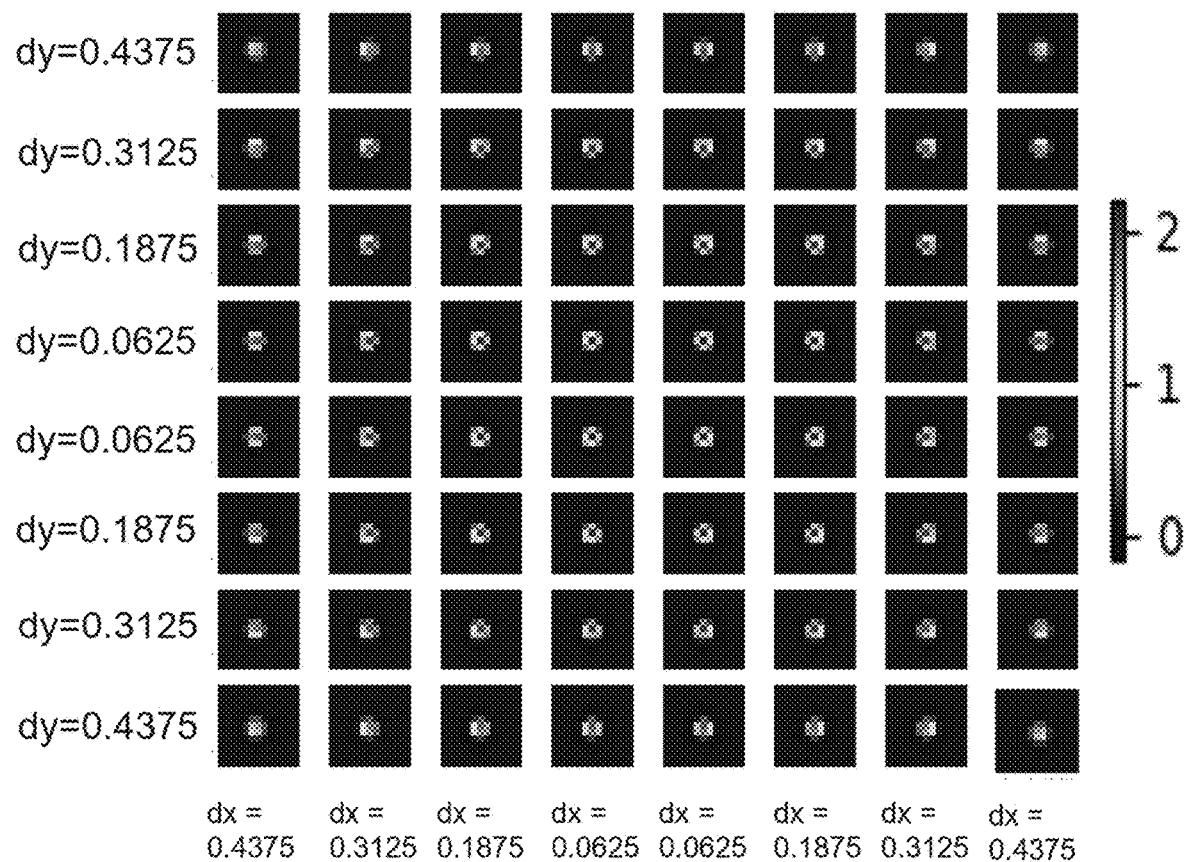
FIG. 7E shows an example of a complete filter bank for one of the fluorescent channels.
Figure 8A:
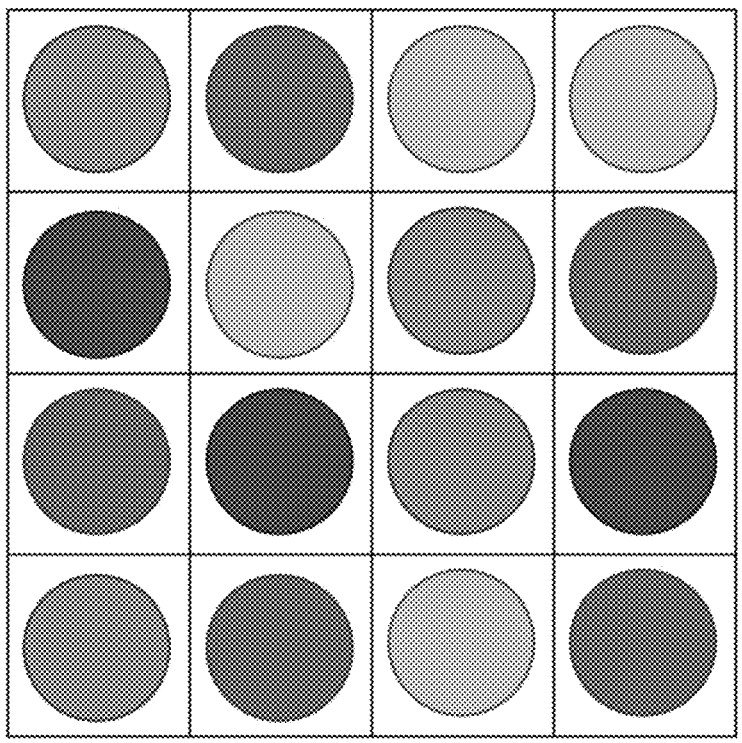
FIGS. 8A-8B show a simplified version of an object having a repeating pattern of features in an xy plane.
Figure 8B:
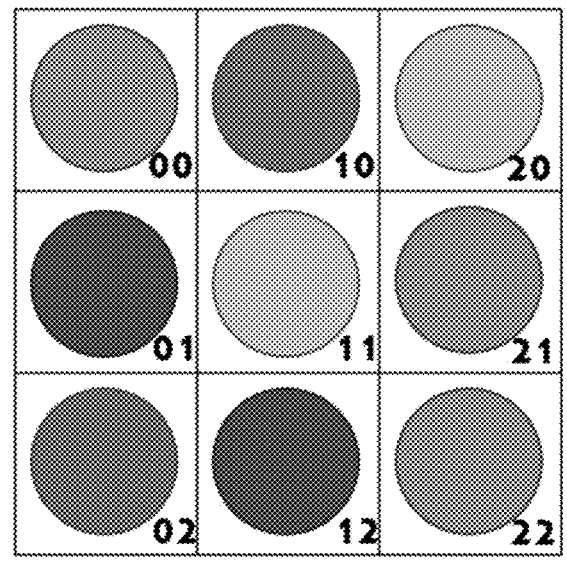

Construction of the inverse filters. We require that the locations of the features to be accurate to within a fraction $\delta<1$ of a pixel. In embodiments, $\delta=\frac{1}{8}$ of a pixel. This implies that that any extraction filter applied to a feature must have its coefficients specific to the location of that feature. The mismatch between the actual feature coordinates and the coordinates assumed by the filter construction must not exceed $\delta$. In order to ensure that this is the case, we construct a bank of $(1/\delta)^2=8*8=64$ filters for each of the emission channels. The filters are chosen from the slices $B^+$(n, :, :). The size of the matrix B (and therefore $B^+$) is chosen large enough so that it contains several thousands of features. This ensures that it has enough diversity of subpixel locations, so that we have enough features to choose from that closely match the subpixel offsets (dx, dy) of each of the 64 bins. An example of a complete filter bank for one of the fluorescent channels is in FIG. 7E.

By construction, the filters are each normalized to sum to 1. The filters derived from the Airy function in theory have infinite support, therefore we must make a choice where to truncate them. The spatial extent of the filters is chosen based on the cutoff criterion, namely we include enough pixels to cover all the filter coefficients with absolute value greater than epsilon. In embodiments, epsilon is equal to $3*10^{-4}$. Another requirement is that the filter is square and the side dimensions are odd. In embodiments, the filter dimensions are e.g. 13×13 pixels, 11×11 pixels, 9×9 pixels or 7×7 pixels.

As mentioned above, the apparent pattern pitch and orientation may deviate somewhat from the nominal due to optical distortion and unit-to-unit variations in magnification, etc. In embodiments, the deviations in apparent pitch are estimated to be about 1%, and all the other sources of variation are estimated to be under 1%. Therefore, the possible worst-case error due to all these effects over half the span of the filter (13/2=6.5 pixels) is about 0.13 pixels, which matches $\delta$. This justifies using a single set of filters based on the nominal pitch to cover all extraction possibilities across the field of view and across copies of the lenses.

Storage and retrieval of filters. The inverse filters are arranged into a filtered bank in computer memory. In embodiments, the filter bank is stored as a 5-dimensional array of floating point numbers dimensions ($N_{channels}$, $1/\delta$, $1/\delta$, 13, 13)=(4, 8, 8, 13, 13). The filter bank can be written to a disk file and retrieved for reuse.

Extraction as sparse convolution. The filters are applied to the image in a manner that can be described as sparse convolution. Instead of applying the filter at every pixel as in standard convolution, we apply the filter only at the feature locations. The filter is multiplied together with a 13×13 window of the image centered on the (properly rounded) coordinates of the feature. Extraction proceeds as a loop over all features. For each feature, the integer parts of the feature x, y coordinates serve as coordinates of the center pixel of the convolution window. The fractional parts of x, y are used to look up the filter in the bank that is appropriate to the sub-pixel position of the feature.

Aggregation of results across the image, across channels, and across cycles. After the extraction has been applied to every color channel image, the resulting intensity arrays c are concatenated into one array for the entire image. Besides the intensities, auxiliary data items are also concatenated in similar-sized array. For example, these items include: feature x and y coordinates, integer indices i and j. All these data items are assembled into a 2D array, where every row corresponds to a feature.

Output of extracted signals. The array with the extracted intensities, coordinates and indices is written to a file on a non-volatile storage medium, e.g. a HDF5 file on a hard disk; one file per tile per cycle. The configuration settings may also be saved in the same file. Alternatively, the array residing in RAM may be directly passed onto the next stage in the processing pipeline, e.g. to a basecaller, without writing it to non-volatile storage.

Example Computer System

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

With certain aspects, to provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such backend, middleware, or front-end components. The components of the system may be interconnected by any form or medium of digital data communication (e.g., a communication network). Examples of communication networks include a local area network ("LAN"), a wide area network ("WAN"), the Internet, WiFi (IEEE 802.11 standards), NFC, BLUETOOTH, ZIGBEE, and the like.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed:

1. A method of quantifying features in a repeating pattern of an object, the method comprising:
obtaining an image of the object using a detection apparatus, wherein the image includes a repeating pattern of features having different signal levels;
providing the image or image-related data to a computer, wherein the computer has parameter data that describe the repeating pattern of features;
partitioning the image or the image-related data into a plurality of registration subimages on the computer;
detecting on the computer the repeating pattern of features for each registration subimage;
assigning an index address for each feature of the repeating pattern of features;
quantifying a signal level of each feature;
wherein a first camera collects an image of a first fluorescent channel and a second fluorescent channel and wherein a second camera collects an image of a third fluorescent channel and a fourth fluorescent channel, and further comprising performing a chromatic correction in order to associate feature images in the channels of a common camera.

2. The method of claim 1, further comprising providing the object, wherein the object has a repeating pattern of features in a two-dimensional plane.

3. The method of claim 2, wherein the object is or relates to genomic fragments immobilized on an array.

4. The method of claim 1, wherein the detection apparatus includes at least one camera.

5. The method of claim 1, wherein the parameter data relates to at least one of a grid orientation angle, an apparent pitch in pixel units, and a phase of a feature grid at a fixed pixel location of the image.

6. The method of claim 1, wherein quantifying the signal level of each feature comprises building a model of the subimage incorporating known feature locations and corresponding unknown intensities and fitting the model to the image of the object.

7. The method of claim 6, wherein the model of the subimage comprises a matrix that is pre-computed and stored in computer memory or a computer-readable medium.

8. The method of claim 7, wherein the matrix is reused for a different subimage.

9. The method of claim 7, wherein each unique address is an integer vector of length 2.

10. The method of claim 1, wherein each index address is a unique address.

11. The method of claim 1, wherein the detection apparatus comprises at least two cameras including the first camera and the second camera and wherein each of the first camera and the second camera is configured to obtain an image of two different color channels.

12. The method of claim 1, wherein each color channel coincides with a different label used to distinguish one nucleotide base type from another nucleotide base type.

13. The method of claim 1, wherein the chromatic correction comprises an affine transform.

14. The method of claim 13, wherein the affine transform is calculated from a maximum intensity projection of an image.

15. A non-transitory computer-readable medium containing instructions to configure a processor to perform operations comprising:
obtaining an image of the object using a detection apparatus, wherein the image includes a repeating pattern of features having different signal levels;
providing the image or image-related data to a computer, wherein the computer has parameter data that describe the repeating pattern of features;
partitioning the image or the image-related data into a plurality of registration subimages on the computer;
detecting on the computer the repeating pattern of features for each registration subimage;
assigning an index address for each feature of the repeating pattern of features;
matching the index address for each feature on the computer; and
quantifying a signal level of each feature;

wherein a first camera collects an image of a first fluorescent channel and a second fluorescent channel and wherein a second camera collects an image of a third fluorescent channel and a fourth fluorescent channel, and the operations further comprising performing a chromatic correction in order to associate feature images in the channels of a common camera.

16. A system comprising:

a processor; and a memory, wherein the processor and the memory are configured to perform operations comprising:

obtaining an image of the object using a detection apparatus, wherein the image includes a repeating pattern of features having different signal levels;

providing the image or image-related data to a computer, wherein the computer has parameter data that describe the repeating pattern of features;

partitioning the image or the image-related data into a plurality of registration subimages on the computer;

detecting on the computer the repeating pattern of features for each registration subimage;

assigning an index address for each feature of the repeating pattern of features;

matching the index address for each feature on the computer; and quantifying a signal level of each feature;

wherein a first camera collects an image of a first fluorescent channel and a second fluorescent channel and wherein a second camera collects an image of a third fluorescent channel and a fourth fluorescent channel, and the operations further comprising performing a chromatic correction in order to associate feature images in the channels of a common camera.

* * * * *